United States Patent
Boylan et al.

(10) Patent No.: US 6,706,053 B1
(45) Date of Patent: Mar. 16, 2004

(54) NITINOL ALLOY DESIGN FOR SHEATH DEPLOYABLE AND RE-SHEATHABLE VASCULAR DEVICES

(75) Inventors: John F. Boylan, Murrieta, CA (US); Scott J. Huter, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/561,747

(22) Filed: Apr. 28, 2000

(51) Int. Cl.$^7$ .............................................. A61M 29/00
(52) U.S. Cl. ...................................................... 606/200
(58) Field of Search ................................ 606/200, 151, 606/157, 113, 114, 159; 623/1.2; 148/421

(56) References Cited

U.S. PATENT DOCUMENTS

| | | |
|---|---|---|
| 4,505,767 A | 3/1985 | Quin |
| 4,580,568 A | 4/1986 | Gianturco |
| 4,665,906 A | 5/1987 | Jervis |
| 4,856,516 A | 8/1989 | Hillstead |
| 4,881,981 A | 11/1989 | Thoma et al. |
| 4,925,445 A | 5/1990 | Sakamoto et al. |
| 5,067,957 A | 11/1991 | Jervis |
| 5,092,877 A | 3/1992 | Pinchuk |
| 5,190,546 A | 3/1993 | Jervis |
| 5,292,331 A | 3/1994 | Boneau |
| 5,341,815 A | 8/1994 | Cofone et al. |
| 5,458,615 A | 10/1995 | Klemm et al. |
| 5,486,183 A | 1/1996 | Middleman et al. |
| 5,514,154 A | 5/1996 | Lau et al. |
| 5,562,641 A | 10/1996 | Flomenblit et al. |
| 5,569,295 A | 10/1996 | Lam |
| 5,597,378 A | 1/1997 | Jervis |
| 5,632,746 A | 5/1997 | Middleman et al. |
| 5,637,089 A | 6/1997 | Abrams et al. |

(List continued on next page.)

FOREIGN PATENT DOCUMENTS

| EP | 0 873 734 | 10/1998 |
|---|---|---|
| WO | WO 99/44542 | 9/1999 |

OTHER PUBLICATIONS

T.W. Duerig et al., *Ti–Ni Shape Memory Alloys,* Advanced Materials, 1035–1048.

Schetky, L. McDonald, *Shape Memory Alloys,* Scientific American, pp. 74–82 (Nov. 1979).

Scott M. Russell et al., *Improved NiTi Alloys For Medical Applications,* Proceedings of the Second International Conference on Shape Memory and Superelastic Technologies, 429–436 (1997).

Duerig, T.W. et al., *An Engineer's Perspective of Pseudoelasticity,* Engineering Aspects of Shape Memory Alloys, pp. 369–393 (1990).

*Primary Examiner*—Michael J. Milano
*Assistant Examiner*—(Jackie) Tan-Uyen T. Ho
(74) *Attorney, Agent, or Firm*—Fulwider Patton Lee & Utecht, LLP

(57) ABSTRACT

An embolic protection device that employs a superelastic alloy self-expanding strut assembly with a small profile delivery system for use with interventional procedures is disclosed. The expandable strut assembly is covered with a filter element and both are compressed into a restraining sheath for delivery to a deployment site downstream and distal to the interventional procedure. Once at the desired site, the restraining sheath is retracted to deploy the embolic protection device, which captures flowing emboli generated during the interventional procedure. The expandable strut assembly is made from a superelastic alloy such as nickel-titanium or nitinol, and includes a ternary element in order to minimize the stress hysteresis of the superelastic material. The stress hysteresis is defined by the difference between the loading plateau stress and the unloading plateau stress of the superelastic material. The resulting delivery system including the restraining sheath has a small profile and has a thin wall.

18 Claims, 3 Drawing Sheets

U.S. PATENT DOCUMENTS

| | | |
|---|---|---|
| 5,643,312 A | 7/1997 | Fischell et al. |
| 5,720,754 A | 2/1998 | Middleman et al. |
| 5,843,244 A | 12/1998 | Pelton et al. |
| 5,885,381 A | 3/1999 | Mitose et al. |
| 5,907,893 A | 6/1999 | Zadno-Azizi et al. |
| 5,927,345 A | 7/1999 | Samson |
| 6,004,330 A | 12/1999 | Middleman et al. |
| 6,051,021 A | 4/2000 | Frid |
| 6,059,810 A | 5/2000 | Brown et al. |
| 6,066,149 A * | 5/2000 | Samson et al. ............. 606/159 |
| 6,086,610 A | 7/2000 | Duerig et al. |
| 6,179,859 B1 * | 1/2001 | Bates et al. ................. 606/114 |
| 6,346,116 B1 * | 2/2002 | Brooks et al. ............. 606/159 |
| 6,428,634 B1 * | 8/2002 | Besselink et al. .......... 148/421 |
| 6,461,453 B1 | 10/2002 | Abrams et al. |

* cited by examiner

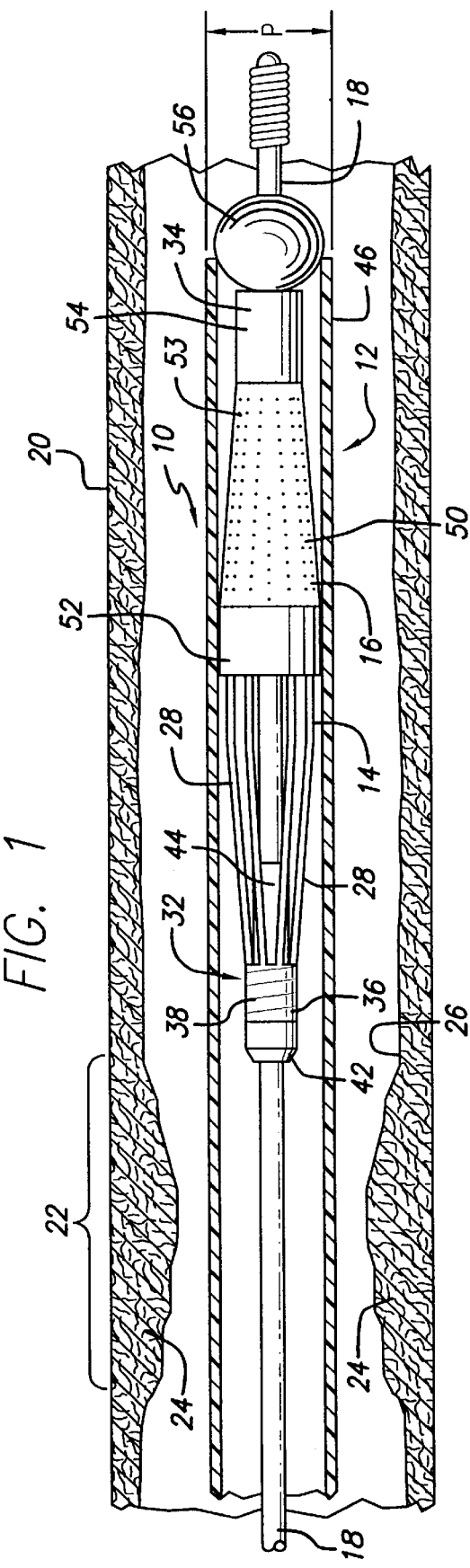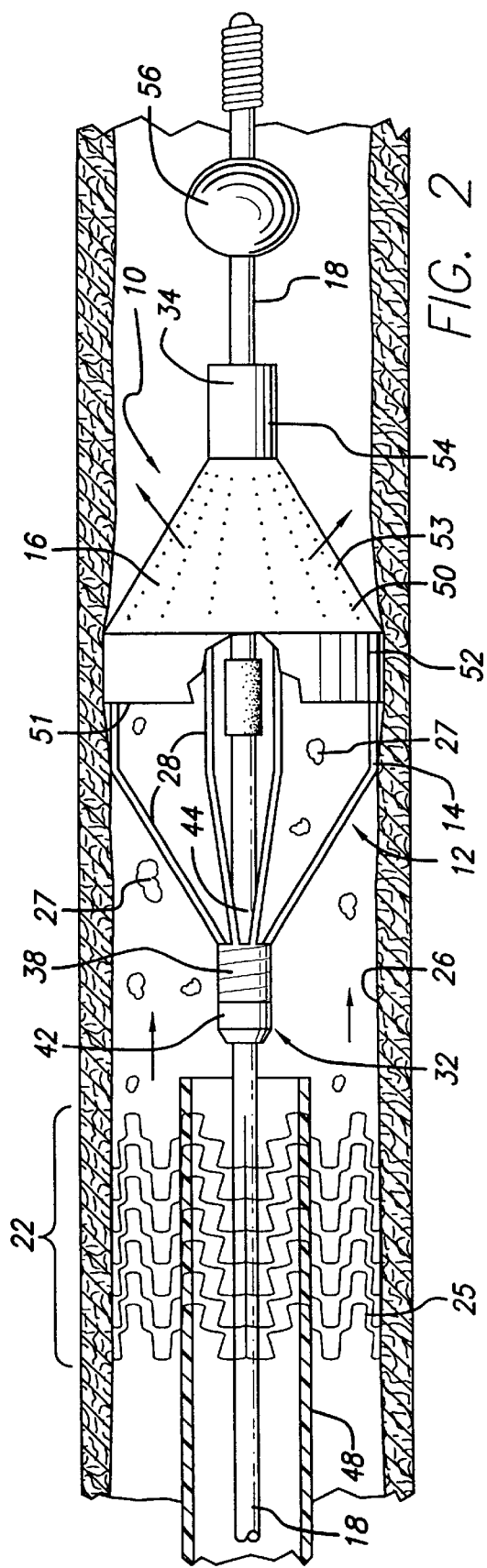

NITINOL ALLOY DESIGN FOR SHEATH DEPLOYABLE AND RE-SHEATHABLE VASCULAR DEVICES

BACKGROUND OF THE INVENTION

The present invention relates generally to filtering devices and systems which can be used when an interventional procedure is being performed in a stenosed or occluded region of a blood vessel to capture embolic material that may be created and released into the bloodstream during the procedure. More precisely, the present invention is directed to filtering devices that include a superelastic metal that is alloyed with a ternary element to obtain a desired hysteresis curve that maximizes performance of the filtering devices.

The embolic filtering devices and systems of the present invention are particularly useful when performing balloon angioplasty, stenting procedures, laser angioplasty or atherectomy in critical vessels, particularly in vessels such as the carotid arteries, where the release of embolic debris into the bloodstream can occlude the flow of oxygenated blood to the brain or other vital organs, which can cause devastating consequences to the patient. While the embolic protection devices and systems of the present invention are particularly useful in carotid procedures, the inventions can be used in conjunction with any vascular interventional procedure in which there is an embolic risk.

A variety of non-surgical interventional procedures have been developed over the years for opening stenosed or occluded blood vessels in a patient caused by the build up of plaque or other substances on the wall of the blood vessel. Such procedures usually involve the percutaneous introduction of the interventional device into the lumen of the artery, usually through a catheter. In typical carotid percutaneous transluminal angioplasty (PTA) procedures, a guiding catheter or sheath is percutaneously introduced into the cardiovascular system of a patient through the femoral artery and advanced through the vasculature until the distal end of the guiding catheter is in the common carotid artery. A guide wire and a dilatation catheter having a balloon on the distal end are introduced through the guiding catheter with the guide wire sliding within the dilatation catheter. The guide wire is first advanced out of the guiding catheter into the patient's carotid vasculature and is directed across the arterial lesion. The dilatation catheter is subsequently advanced over the previously advanced guide wire until the dilatation balloon is properly positioned across the arterial lesion. Once in position across the lesion, the expandable balloon is inflated to a predetermined size with a radiopaque liquid at relatively high pressures to radially compress the atherosclerotic plaque of the lesion against the inside of the artery wall, thereby dilating the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

Another procedure is laser angioplasty which uses a laser to ablate the stenosis by super heating and vaporizing the deposited plaque. Atherectomy is yet another method of treating a stenosed blood vessel in which cutting blades are rotated to shave the deposited plaque from the arterial wall. A vacuum catheter is usually used to capture the shaved plaque or thrombus from the blood stream during this procedure.

In the procedures of the kind discussed above, abrupt reclosure or restenosis of the artery may occur over time, which may then require another angioplasty procedure, a surgical bypass operation, or some other method of repairing or strengthening the stenosed area. To reduce the likelihood of the occurrence of abrupt reclosure and to strengthen the area, a physician can implant an intravascular prosthesis, commonly known as a stent, for maintaining vascular patency inside the artery across the lesion. The stent is crimped tightly onto the balloon portion of a catheter and transported in its delivery diameter through the patient's vasculature. At the deployment site, the stent is expanded to a larger diameter, often by inflating the balloon portion of the catheter.

Prior art stents typically fall into two general categories of construction. The first type of stent is expandable upon application of a controlled force, as described above, through the inflation of the balloon portion of a dilatation catheter which, upon inflation of the balloon or other expansion means, expands the compressed stent to a larger diameter to be left in place within the artery at the target site.

The second type of stent is a self-expanding stent formed from, for example, shape memory or superelastic alloys including nickel-titanum (NiTi) alloys, which automatically expand from a collapsed state when the stent is advanced out of the distal end of the delivery catheter into the body lumen. Such stents manufactured from expandable heat sensitive materials allow for phase transformations of the material to occur, resulting in the expansion and contraction of the stent.

The above non-surgical, interventional procedures when successful avoid the necessity of major surgical operations. However, there is one common problem associated with all of these non-surgical procedures. Namely, the potential release of embolic debris into the bloodstream can occlude the distal vasculature and cause significant health problems for the patient. In one example, during deployment of a stent, it is possible that the metal struts of the stent cut into the stenosis and shear off pieces of plaque which become embolic debris that travel downstream and lodge somewhere in the patient's vascular system. In another example, pieces of plaque can sometimes dislodge from the stenosis during a balloon angioplasty procedure and become released into the bloodstream. In yet another example, while complete vaporization of plaque is the intended goal during a laser angioplasty procedure, quite often particles are not fully vaporized and thus enter the bloodstream. Likewise, not all of the emboli created during an atherectomy procedure are drawn into the vacuum catheter and, as a result, enter the bloodstream as well.

When any of the above-described procedures are performed in the carotid or like arteries, the release of emboli into the circulatory system can be extremely dangerous and sometimes fatal to the patient. Debris that is carried by the bloodstream to distal vessels of the brain can cause these cerebral vessels to occlude, resulting in a stroke, and in some cases, death. Therefore, although cerebral percutaneous transluminal angioplasty has been performed in the past, the number of procedures performed has been limited due to the justifiable fear of causing an embolic stroke.

Medical devices have been developed in an effort to resolve the problem created when debris or fragments enter the circulatory system following vessel treatment using any one of the above-identified procedures. One approach which has had some limited success is the placement of a filter or trap downstream from the treatment site to capture embolic debris before it reaches the smaller blood vessels downstream. Again, there have been problems associated with such filtering systems, particularly during the expansion and collapse of the filter within the body vessel. If the filtering device does not have a suitable mechanism for closing the filter, there is a possibility that trapped embolic debris can backflow through the inlet opening of the filter and enter the bloodstream as the filtering system is collapsed and removed from the patient. The backflow is caused by the act of collapsing the filter device, which then squeezes trapped embolic material through the opening of the filter and back into the bloodstream.

Many of the prior art filters that can be expanded within a blood vessel are attached to the distal end of a guide wire or guide wire-like tubing. The guide wire or guide wire-like tubing allows the filtering device to be placed in the patient's vasculature when the guide wire is manipulated in place. Once the guide wire is in proper position in the vasculature, the embolic filter can be deployed within the vessel to capture embolic debris. The guide wire can then be used by the physician to deliver interventional devices, such as a balloon angioplasty dilatation catheter or a stent, into the area of treatment.

What has been needed is a reliable filtering device and system for use when treating stenosis in blood vessels which helps prevent the risk when embolic debris that can cause blockage in vessels at downstream locations is released into the bloodstream. The device should be capable of filtering any embolic debris which may be released into the bloodstream during the treatment and safely contain the debris until the filtering device is to be collapsed and removed from the patient's vasculature. The device should be relatively easy for a physician to use and should provide a failsafe filtering device that captures and removes any embolic debris from the bloodstream. Moreover, such a device should be relatively easy to deploy and remove from the patient's vasculature. Such important applications as mentioned above have prompted designers of embolic filtering devices to use superelastic or shape memory alloys in their designs to exploit the materials' properties.

Although not directed to embolic protection devices, an example of shape memory alloy as applied to stents is disclosed in, for example, European Patent Application Publication No. EP0873734A2, entitled "Shape Memory Alloy Stent." This publication suggests a stent for use in a lumen in a human or animal body having a generally tubular body formed from a shape memory alloy which has been treated so that it exhibits enhanced elastic properties. In particular, in the stress-strain curve exhibiting loading and unloading of the shape memory alloy material, the applicant suggests using a composition that results in a large difference between the loading and unloading curves, otherwise known as a wide hysteresis.

The wide hysteresis means that the inward force required to compress the stent transversely once in place in the lumen is relatively high, while the outward force that the stent exerts on the lumen as it attempts to revert to its original undeformed configuration is relatively low. This can mean that the lumen is resistant to being crushed by externally applied forces which can be a problem for lumens close to the surface such as arteries in the thigh and neck. The publication further suggests use of specified ternary elements in a nickel titanium alloy to obtain a stent exhibiting a wider hysteresis in the stress-strain behavior in a loading and unloading cycle.

The evolution of superelastic and shape memory alloy devices progressed to use of ternary elements in combination with nickel and titanium to obtain specific material properties. Use of a ternary element in a superelastic stent, as opposed to embolic protection devices, is shown in, for example, U.S. Pat. No. 5,907,893 to Zadno-Azizi et al. As a general proposition, there have been attempts at adding a ternary element to nickel-titanium alloys as disclosed in, for instance, U.S. Pat. No. 5,885,381 to Mitose et al.

The conventional efforts of using a ternary element in a superelastic material for a stent have focused only on a wider hysteresis in the stress-strain behavior in a loading or unloading cycle of the stent. Unfortunately, the greater the difference between the loading and unloading stress plateaus, the stronger the delivery system must be to accommodate any given level of stent performance. Typically, a stronger delivery system must also be larger and bulkier. This is a major drawback to conventional superelastic stents and delivery systems when the stent must be delivered through tortuous vessels at remote locations in the human anatomy.

What has been needed and heretofore unavailable in the prior art is a superelastic, removable filtering device and delivery system that apply a ternary element to the superelastic alloy in order to minimize the hysteresis. That hysteresis is defined by the difference between the loading and unloading plateau stresses of the material as plotted on a stress-strain curve.

SUMMARY OF THE INVENTION

The present invention is generally directed to a number of filtering devices and systems for capturing embolic debris in a blood vessel created during the performance of a therapeutic interventional procedure, such as a balloon angioplasty or stenting procedure, in order to prevent the embolic debris from blocking blood vessels downstream from the interventional site. The devices and systems of the present invention are particularly useful while performing an interventional procedure in critical arteries, such as the carotid arteries, in which vital downstream blood vessels can easily become blocked with embolic debris, including the main blood vessels leading to the brain. When used in carotid procedures, the present invention minimizes the potential for a stroke occurring during the procedure. As a result, the present invention provides the physician with a higher degree of confidence that embolic debris is being properly collected and removed from the patient's vasculature during the interventional procedure.

An embolic protection device and system made in accordance with the present invention includes an expandable filter assembly which is affixed to the distal end of a cylindrical shaft, such as a guide wire. The filter assembly includes an expandable strut assembly preferably made from a self-expanding material, such as a nickel-titanium (NiTi) alloy, and includes a number of outwardly biased and extending struts that are capable of self-expansion from a contracted or collapsed position to an expanded or deployed position within the patient's vasculature. A filter element made from an embolic capturing media is attached to the expandable strut assembly. The filter element opens from a collapsed configuration to an expanded configuration via the movement of the expandable struts similar to that of an umbrella.

In particular, the expandable strut assembly of the filter assembly includes a superelastic alloy, wherein the alloy optionally includes a ternary element, and wherein the alloy further includes a substantially small stress hysteresis; and a delivery system including a sheath having a distal end and a proximal end, wherein the filter assembly is disposed inside the sheath at the distal end, and wherein the sheath has a small profile.

In an exemplary embodiment, the superelastic alloy includes binary nickel-titanium alloys that exhibit superelasticity and have an unusual stress-strain relationship. More precisely, the superelastic curve is characterized by regions of nearly constant stress upon loading (referred to as the loading plateau stress) and unloading (unloading plateau stress). The loading plateau stress is always larger than the unloading plateau stress. The loading plateau represents the period during which martensite is being stress-induced in favor of the original austenitic structure. As the load is removed, the stress-induced martensite transforms back into austenite along the unloading plateau.

The superelastic, self-expanding strut assembly of the present invention filter assembly is collapsed (that is, loaded) and then constrained within a delivery system such as a restraining sheath. At the point of delivery, the restraining sheath is retracted and the filter assembly is released (that is, unloaded) and allowed to reassume its original diameter and shape. The filter assembly is designed to perform various mechanical functions within the lumen, all of which are based upon the lower unloading plateau stress.

Importantly, according to the present invention, a preferred lower loading plateau stress relative to the unloading plateau stress of the superelastic material in the self-expanding strut assembly establishes the mechanical resistance the assembly exerts against the delivery system. The superelastic material of the self-expanding strut assembly of the present invention further exhibits a small hysteresis and a relatively high unloading plateau stress. The small stress hysteresis defined by the loading and unloading stress plateaus is preferably accomplished by using a ternary element in addition to the superelastic alloy.

As a result, the present invention filter assembly and delivery system enjoy an overall reduced delivery system profile for any given level of filter assembly mechanical performance. Moreover, because of the smaller hysteresis and lower loading plateau stress relative to the unloading plateau stress for a given level of performance, the delivery system including the sheath can be made of a thinner wall material, leading to better flexibility.

In addition, the smaller hysteresis and lower loading plateau stress ensure easy collapse and retraction of the filter assembly into the delivery system. To be sure, as part of the delivery system, the recovery sheath used to collapse the deployed filter assembly can have a smaller profile with a thinner wall, again improving overall flexibility of the system.

The present invention is therefore superior to a system that relies on a wide hysteresis curve. The greater the difference between the two plateau stresses is, the wider the hysteresis curve, and the stronger the delivery system must be to accommodate any given level of self-expanding strut performance. A stronger delivery system entails a bulkier, larger profile device. The device by its bulky nature is more inflexible, leading to difficulties in accessing remote lesions.

As mentioned above, a preferred superelastic alloy is nickel-titanium or nitinol. In the exemplary embodiment, the ternary element may be palladium, platinum, chromium, iron, cobalt, vanadium, manganese, boron, copper, aluminum, tungsten, tantalum, or zirconium.

Other features and advantages of the present invention will become more apparent from the following detailed description of the invention when taken in conjunction with the accompanying exemplary drawings.

BRIEF DESCRIPTION OF THE DRAWINGS

FIG. 1 is an elevational view, partially in cross-section, of an embolic protection device embodying features of the present invention showing the expandable filter assembly in its collapsed position within a restraining sheath and disposed within a vessel.

FIG. 2 is an elevational view, partially in cross-section, similar to that shown in FIG. 1, wherein the expandable filter assembly is in its expanded position within the vessel.

DETAILED DESCRIPTION OF THE PREFERRED EMBODIMENTS

Figure 3:
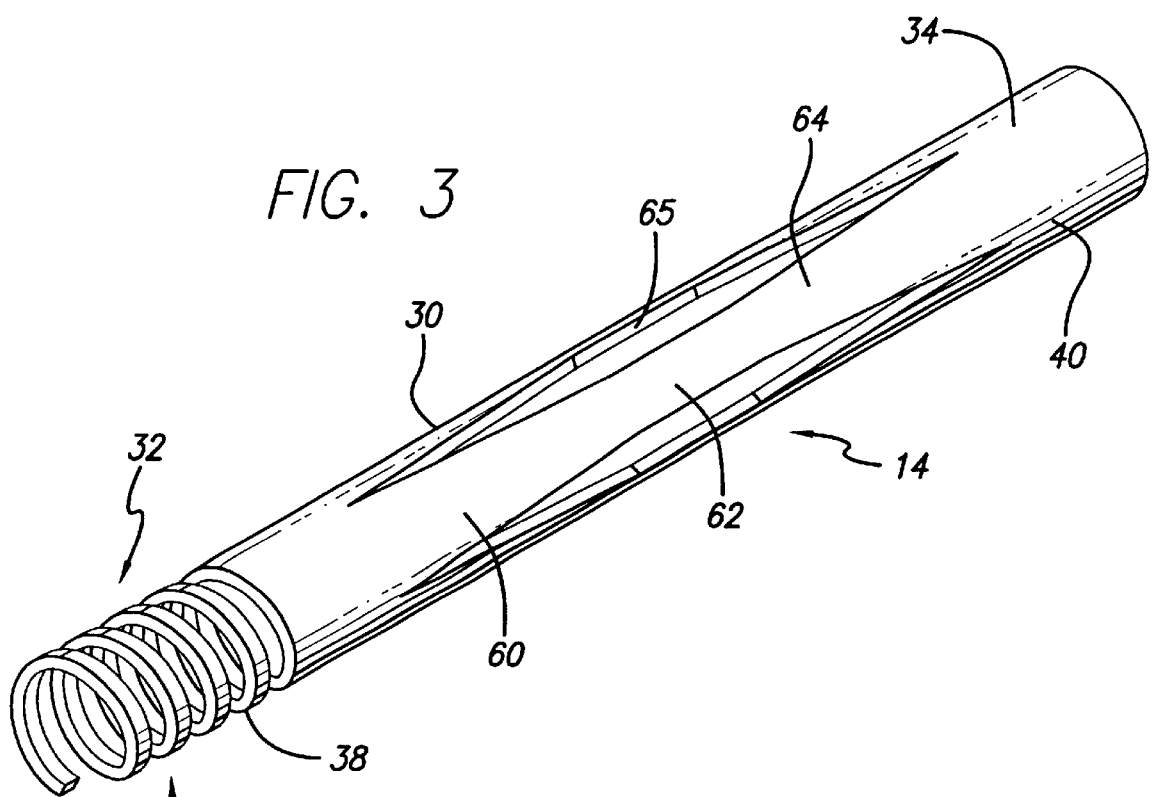
FIG. 3 is a perspective view of an expandable strut assembly which forms part of the filter assembly of the present invention as shown in its collapsed position.

The present invention is generally directed to a filtering device and system for capturing embolic debris in a blood vessel created during the performance of a therapeutic interventional procedure, such as a balloon angioplasty or stenting procedure, in order to prevent the embolic debris from blocking blood vessels downstream from the interventional site. In a preferred embodiment, the present invention filtering device incorporates superelastic alloys conferring a small hysteresis curve with high level loading and unloading plateau stresses.

Turning now to the drawings, in which like reference numerals represent like or corresponding elements, FIGS. 1 and 2 illustrate a preferred embodiment embolic protection device 10 incorporating features of the present invention. In the particular embodiment shown in FIGS. 1 and 2, the embolic protection device 10 is constructed from a filter assembly 12, which includes an expandable strut assembly 14 and a filter element 16. The filter assembly 12 is rotatably mounted on the distal end of an elongated tubular shaft, such as a guide wire 18, for example.

In the side elevational and cross-sectional views of FIGS. 1 and 2, the embolic protection device 10 is shown positioned within an artery 20 or other blood vessel of a patient. This portion of the artery 20 has an area of treatment 22 in which atherosclerotic plaque 24 has built up against the inside wall 26 of the artery 20. The filter assembly 12 is placed distal to, and downstream from, the area of treatment 22.

A balloon angioplasty catheter (not shown) can be introduced within the patient's vasculature in a conventional Seldinger technique through a guiding catheter (not shown). The guide wire 18 is passed through the area of treatment 22 and the dilatation catheter can be advanced over the guide wire 18 within the artery 20 until the balloon portion is appositioned directly in the area of treatment 22. The balloon of the dilatation catheter is inflated, thereby expanding the plaque 24 against the inside wall 26 of the artery 20. This opens the occlusion, expands the artery 20, and reduces the blockage in the vessel caused by the plaque 24.

After the dilatation catheter is removed from the patient's vasculature, a stent 25 (shown in FIG. 2) may be delivered to the area of treatment 22 using over-the-wire techniques. The stent 25 helps to scaffold and maintain the area of treatment 22, which in turn help to prevent restenosis from occurring in the area of treatment 22.

Any embolic debris 27 that breaks off from the plaque 24 during the interventional procedure is released into the bloodstream. The embolic debris 27 is carried by blood flow (indicated by arrows) and is captured by the deployed, i.e., unfurled, filter element 16 of the filter assembly 12 located downstream from the area of treatment 22. Once the interventional procedure is completed, the filter assembly 12 is collapsed and removed from the patient's vasculature, taking with it all embolic debris 27 trapped within the filter element 16.

One exemplary embodiment of the expandable strut assembly 14 is shown in FIGS. 1–2. As can be seen in these figures, the expandable strut assembly 14 includes a plurality of radially expandable struts 28 that can move from a compressed or collapsed position as shown in FIG. 1 to an expanded or deployed position shown in FIG. 2.

The expandable strut assembly 14 is preferably made from a superelastic material so that the struts 28 have a radially outward bias toward the expanded position. In the preferred embodiment, the superelastic material is a nickel-titanium alloy combined with a ternary element. The alloy is discussed in greater detail below.

The expandable strut assembly 14 includes a proximal end 32 which is optionally rotatably attached to the guide wire 18. A distal end 34 is free to slide longitudinally along the guide wire 18 and can rotate thereabout. The distal end 34 translates along the guide wire 18 whenever the struts 28 move between the expanded and contracted positions. A proximal end 32 includes a short tubular segment or sleeve 36 which has a coil spring formed therein, and which acts as a dampening member or element 38. The function of the dampening element 38 is explained below. The distal end 34 of the tubing 30 preferably includes a short segment or sleeve 40 which is slidably and rotatably disposed on the guide wire 18.

The filter element 16 in one preferred embodiment of the invention includes a tapered or cone shaped section 50, as seen in FIGS. 1 and 2. The filter element 16 optionally has a plurality of openings 53 that allow the blood to perfuse through (indicated by arrows), yet the openings 53 are small enough that the embolic debris 27 is captured inside the cone shaped section 50. The filter element 16 includes a short proximal section 52 which is integral with the cone shaped section 50 and expands to a substantially cylindrical shape when the struts 28 of strut assembly 14 are deployed. An inlet opening 51 located at the short proximal section 52 of cone shaped section 50 collects embolic debris 27, directing the debris 27 into the filter element 16.

The short proximal section 52 also functions as a superstructure to which the filter element 16 and the struts 28 of the strut assembly 14 can be adhesively or otherwise affixed. At the opposite end, the filter element 16 has a short distal cylindrical section 54 which is integral with the remaining sections of the filter element and is attached to the distal end 34 of the expandable strut assembly 14.

As best seen in FIG. 1, the filter assembly 12 is maintained in its collapsed or compressed position through the use of a restraining sheath 46. The restraining sheath 46 should have sufficient elasticity to resist the outward bias of the struts 28. One manner of achieving the required elasticity is through selection of the proper size and wall thickness for the sheath 46. Another is through use of the proper elastic material that has sufficient resilience to resist the expansive forces of the struts 28 held therein. Such sheath materials and designs are known in the art.

Although not shown, the guide wire and the restraining sheath 46 have proximal ends that extend outside of the patient. As such, the struts 28 can be manipulated into the expanded position by retracting the restraining sheath 46 via its proximal end to expose the struts 28. Since the struts 28 are self-expanding by nature, the withdrawal of the restraining sheath 46 allows the struts 28 to spring open and the filter element 16 to unfurl into their expanded positions within the artery 20. This is depicted in FIG. 2.

The guide wire 18 optionally includes a small sphere 56 affixed thereto. The small sphere 56 is useful during the delivery of the embolic protection device 10 into the patient's vasculature. Specifically, the sphere 56 is approximately as large as the inner diameter of the restraining sheath 46 and is effectively used as a nose cone. The nose cone prevents possible "snowplowing" of the embolic protection device 10 as it is delivered through the patient's arteries.

When the embolic protection device 10 is to be removed from the patient's vasculature, a recovery sheath 48 is used to collapse and recover the filter assembly 12, as shown in FIG. 2. Generally, this recovery sheath 48 has a slightly larger inner diameter than the restraining sheath 46 since the struts 28 are now deployed. Furthermore, the recovery sheath 48 must have sufficient tensile strength and elasticity at the distal end 47 to be capable of collapsing the expanded strut assembly 14.

The collapse of the expandable strut assembly 14 can be accomplished by holding the guide wire 18 and moving the proximal end (not shown) of the recovery sheath 48 forward, which moves the distal end 47 of the sheath 48 over the struts 28. Alternatively, the recovery sheath 48 can be held stationary while the proximal end of the guide wire 18 is retracted back to pull the entire filter assembly 12 into the sheath 48. Upon collapse of the filter assembly 12, any embolic debris 27 generated and entering the bloodstream during the interventional procedure remains trapped inside the filter element 16 and is withdrawn from the bloodstream when the embolic protection device 10 is removed from the patient's vasculature.

The number of struts 28 formed on the expandable strut assembly 14 can be any number which provides sufficient expandability within the artery to properly deploy and maintain the filter element 16 in place. In the embodiment shown in FIGS. 1 and 2, the expandable strut assembly has four self-expanding struts 28. Likewise, the particular size and shape of each strut 28 can be varied.

Figure 4:
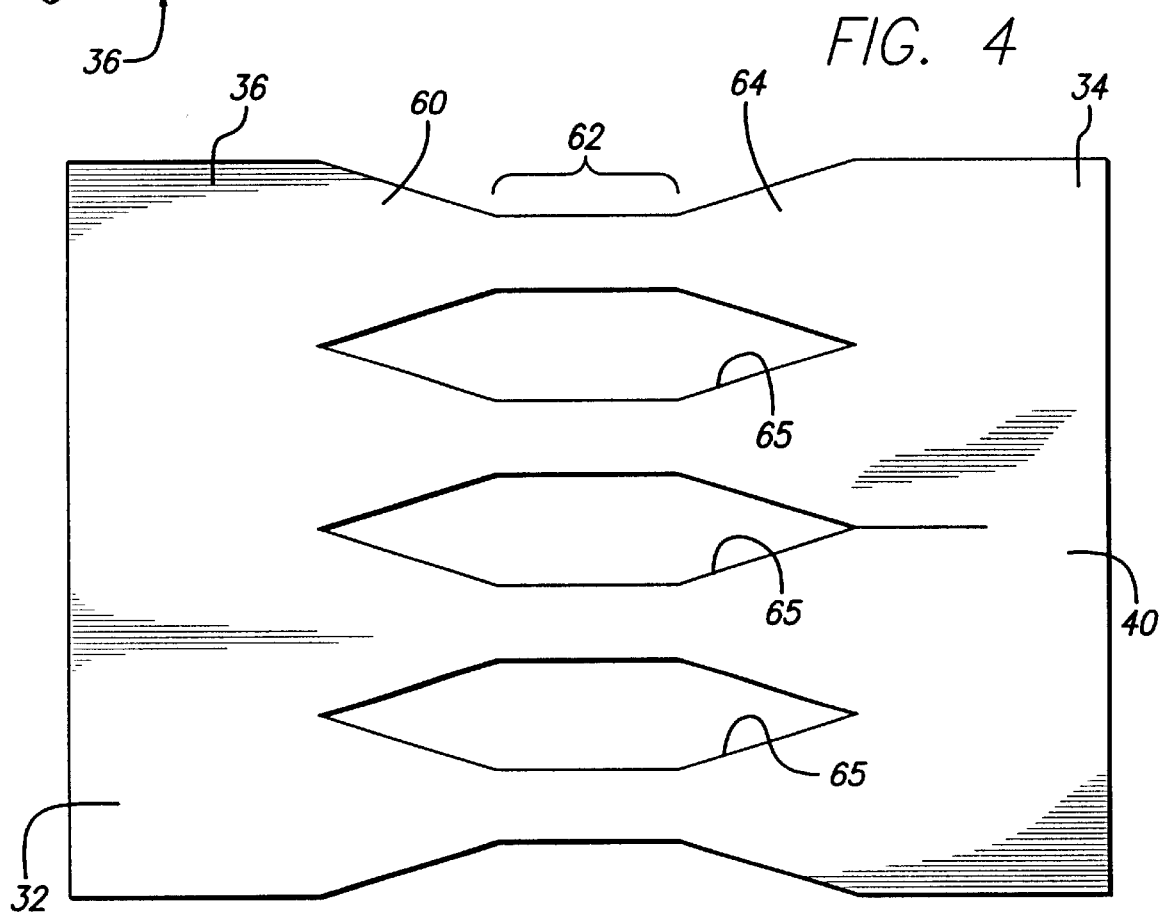
FIG. 4 is a plan view of a flattened section of the expandable strut assembly shown in FIG. 3 which illustrates one particular strut pattern.

FIGS. 3–4 show an expandable strut assembly 14 having a strut pattern formed from an inverted, triangular shape first portion 60, a substantially straight center section 62, and a second inverted triangular shaped section 64, which completes the strut. This particular strut pattern is one preferred design that provides greater strength in regions of the strut where there would be a tendency for the strut to break or become weakened. These regions include the very proximal and distal ends of each strut which are designed with a wider base. This particular design also allows the expandable strut assembly 14 to open and close more uniformly. This is advantageous especially when collapsing the struts for removal from the patient. Additionally, the center section 62 allows the struts 28 to expand to a greater volume, which allows a larger filter element to be placed on the strut assembly 14, if needed.

When the precise pattern is cut into the tubing 30, a sleeve 36 which forms the proximal end 32 may optionally be formed into a helical coil as shown in FIG. 3.

The helical coil then functions as a damping element 38 for the expandable strut assembly 14. As seen in FIGS. 1 and 2, the sleeve 36 slides over the guide wire 18. The proximal end 32 of the expandable strut assembly 14 is mounted between a tapered fitting 42 and an optional radiopaque marker band 44. The tapered end fitting 42 and the marker band 44 affix the proximal end 32 on to the guide wire 18 to prevent any longitudinal motion, yet allow for rotation of the filter assembly 12.

FIG. 4 is a plan view of a rolled out flat sheet of the tubing 30 used to form the struts 28. A particular design pattern is cut into the wall of the tubing 30 in order to form each strut. In the case of the embodiment shown in FIG. 3, that pattern consists of a truncated diamond shape 65 which helps form the first section 60, the center section 62 and the triangular shaped section 64. By selectively removing portions of the tubing 30 through laser cutting, etching, stamping, or other suitable means, each particular strut can be fashioned into a precise shape, width, and length. This truncated diamond pattern 68 repeats, as seen in FIG. 4, to provide uniform size to each of the struts 28 formed therein. Narrow struts such as that shown in FIGS. 1 and 2 can, of course, be formed as described above.

In a preferred embodiment, the expandable strut assembly 14 of the present invention is formed partially or completely of alloys such as nitinol (NiTi) which have superelastic (SE) characteristics. Superelastic alloys are preferably chosen for their elastic behavior, which as explained above, is used to deploy the filter element 16.

The exemplary expandable strut assembly 14 of the present invention includes a superelastic material. More precisely, the term "superelastic" refers to an isothermal transformation—that is, stress inducing a martensitic phase from an austenitic phase. Alloys having superelastic properties generally have at least two phases: a martensitic phase, which has a relatively low tensile strength and which is stable at relatively low temperatures, and an austenitic phase, which has a relatively high tensile strength and which is stable at temperatures higher than the martensitic phase.

Superelastic characteristics generally allow the expandable strut assembly 14 to be deformed by collapsing the self-expanding struts 28, thus creating stress which causes the NiTi to change to the martensitic phase. The expandable strut assembly 14 is restrained in the deformed condition by the delivery or restraining sheath 46 to facilitate the insertion into a patient's body, with such deformation causing the phase transformation. Once within the body lumen, the compressive forces of the restraining sheath 46 on the expandable strut assembly 14 are removed, thereby reducing the stress therein so that the superelastic expandable strut assembly 14 can return to its original, undeformed shape by the transformation back to the austenitic phase.

After the filter assembly 12 has performed its function of capturing free flowing embolic debris 27 or other friable matter, the filter assembly 12 is withdrawn from the patient. Prior to this withdrawal, the recovery sheath 48 is translated distally over the filter assembly 12; or alternatively, the filter assembly 12 is pulled proximally into the recovery sheath 48. In either case, the deployed struts 28 of the expandable strut assembly 14 are collapsed by the elastic forces of the recovery sheath 48. During this collapse, the applied stress to the deployed struts 28 changes their structure from an austenitic to a martensitic phase.

FIG. 1 also depicts a delivery system having a small delivery profile P. This reduced profile P is an advantage of the present invention filter assembly 14 and delivery system (restraining sheath 46 and recovery sheath 48) as a result of the stress-strain hysteresis curve of the superelastic material being minimized. This novel approach is described more fully below.

The expandable strut assembly 14 is preferably formed from a superelastic material such as NiTi and undergoes an isothermal transformation when stressed. The expandable strut assembly 14 and its struts 28 are first compressed to a delivery diameter, thereby creating stress in the NiTi alloy so that the NiTi is in a martensitic state having relatively low tensile strength. While still in the martensitic phase, the filter assembly 12 is inserted into the restraining sheath 46 for delivery to area of treatment 22. The NiTi expandable strut assembly 14 tends to spring back to a larger diameter, and pushes radially outwardly against the inside diameter of the restraining sheath 46.

In its delivery diameter P, the overall diameter of the filter assembly 12 and its restraining sheath 46 is less than the inside diameter of the artery 20 or the vessel in which they are inserted. After the filter assembly 12 is delivered to the artery 20 or other vessel, the stress exerted by the struts 28 may be released by withdrawing restraining sheath 46 in a proximal direction, whereupon struts 28 immediately expand and return toward their original, undeformed shape by transforming back to the more stable austenitic phase.

When stress is applied to a specimen of a metal such as nitinol exhibiting superelastic characteristics at a temperature at or above that which the transformation of the martensitic phase to the austenitic phase is complete, the specimen deforms elastically until it reaches a particular stress level where the alloy then undergoes a stress-induced phase transformation from the austenitic phase to the martensitic phase. As the phase transformation progresses, the alloy undergoes significant increases in strain with little or no corresponding increases in stress. The strain increases while the stress remains essentially constant until the transformation of the austenitic phase to the martensitic phase is complete. Thereafter, further increase in stress is necessary to cause further deformation. The martensitic metal first yields elastically upon the application of additional stress and then plastically with permanent residual deformation.

If the load on the specimen is removed before any permanent deformation has occurred, the martensite specimen elastically recovers and transforms back to the austenitic phase. The reduction in stress first causes a decrease in strain. As stress reduction reaches the level at which the martensitic phase transforms back into the austenitic phase, the stress level in the specimen remains essentially constant (but less than the constant stress level at which the austenitic crystalline structure transforms to the martensitic crystalline structure until the transformation back to the austenitic phase is complete); i.e., there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as superelasticity.

The prior art makes reference to the use of metal alloys having superelastic characteristics in medical devices which are intended to be inserted or otherwise used within a patient's body. See, for example, U.S. Pat. No. 4,665,905 (Jervis) and U.S. Pat. No. 4,925,445 (Sakamoto et al.).

Figure 5:
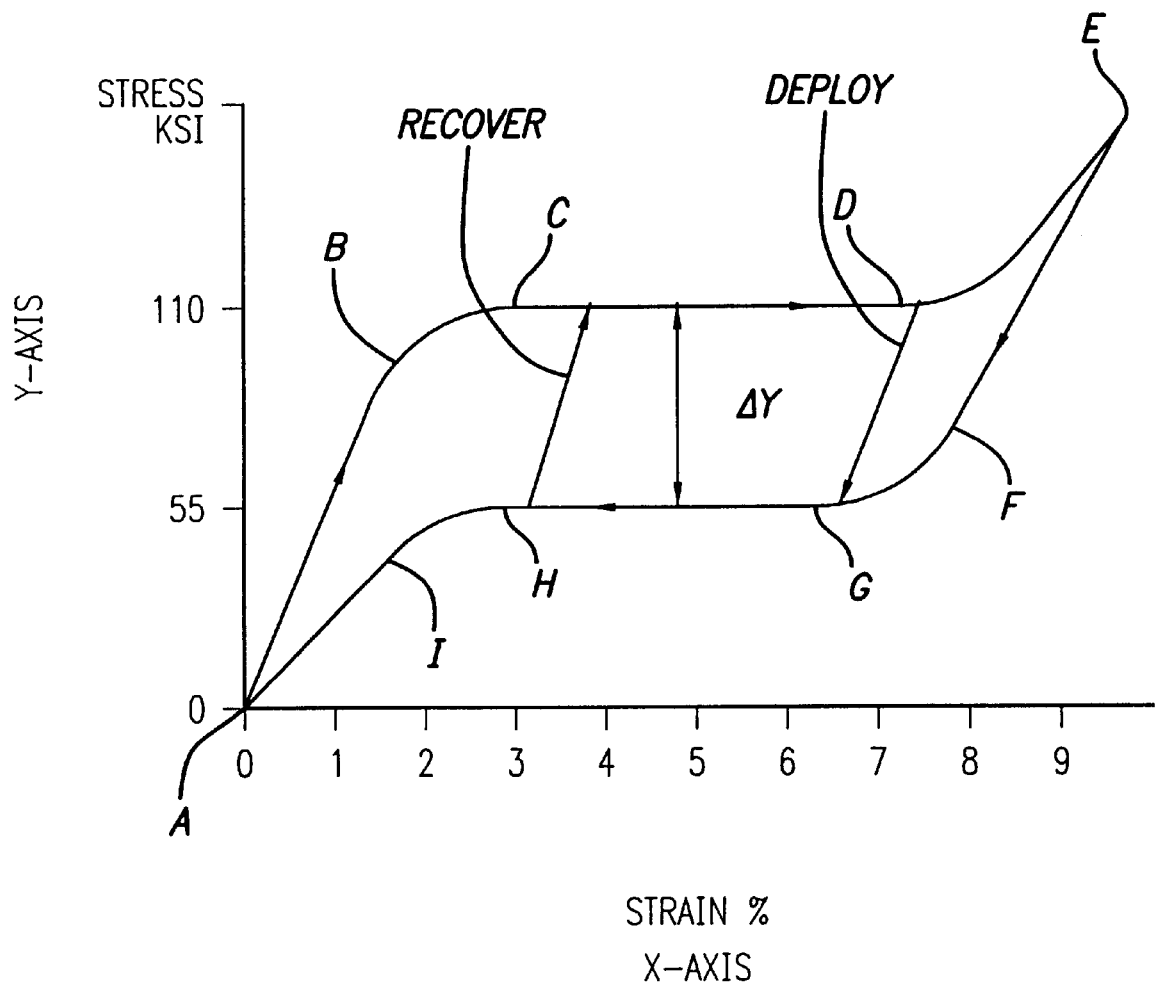
FIG. 5 is a typical stress-strain curve for a superelastic material.

FIG. 5 illustrates an example of a preferred stress-strain relationship of an alloy specimen, such as an expandable strut assembly 14, having superelastic properties as would be exhibited upon tensile testing of the specimen. The relationship is plotted on x-y axes, with the x axis representing strain and the y axis representing stress. For ease of illustration, the x-y axes are labeled with typical pseudoelastic nitinol stress from 0 to 110 ksi and strain from 0 to 9 percent, respectively.

Looking at the plot itself in FIG. 5, the line from point A to point B represents the elastic deformation of the specimen. After point B the strain or deformation is no longer proportional to the applied stress and it is in the region between point B and point C that the stress-induced transformation of the austenitic phase to the martensitic phase begins to occur. There also can be an intermediate phase, called the rhombohedral phase, depending upon the composition of the alloy.

At point C moving toward point D, the material enters a region of relatively constant stress with significant deformation or strain. This constant or plateau region is known as the loading stress, since it represents the behavior of the material as it encounters continuous increasing strain. It is in this plateau region CD that the transformation from austenite to martensite occurs.

At point D the transformation to the martensitic phase due to the application of stress to the specimen is substantially complete. Beyond point D the martensitic phase begins to deform, elastically at first, but, beyond point E, the deformation is plastic or permanent.

When the stress applied to the superelastic metal is removed, the material behavior follows the curve from point E to point F. Within the E to F region, the martensite recovers its original shape, provided that there was no permanent deformation to the martensitic structure. At point F in the recovery process, the metal begins to transform from the stress-induced, unstable, martensitic phase back to the more stable austenitic phase.

In the region from point G to point H, which is also an essentially constant or plateau stress region, the phase transformation from martensite back to austenite takes place. This constant or plateau region GH is known as the unloading stress. The line from point I to the starting point A represents the elastic recovery of the metal to its original shape.

Binary nickel-titanium alloys that exhibit superelasticity have an unusual stress-strain relationship as just described and as plotted in the curve of FIG. 5. As emphasized above, the superelastic curve is characterized by regions of nearly constant stress upon loading, identified above as loading plateau stress CD and unloading plateau stress GH. Naturally, the loading plateau stress CD is always larger than the unloading plateau stress GH. The loading plateau stress represents the period during which martensite is being stress-induced in favor of the original austenitic crystalline structure. As the load is removed, the stress-induced martensite transforms back into austenite along the unloading plateau stress part of the curve.

FIG. 5 is also useful for explaining the different approaches to defining the hysteresis. In one approach, the difference between the stress values at loading plateau stress CD and unloading plateau stress GH defines the hysteresis of the system. This difference is identified as $\Delta y$ of the curve in FIG. 5. If the loading plateau stress CD is at 110 ksi and the unloading plateau stress GH is at 55 ksi, then the $\Delta y$ of the curve is the difference between 110 and 55, which is 55 ksi. Under this approach, $\Delta y$ of the curve is defined as an "absolute" difference in stress plateau values. This absolute difference definition of $\Delta y$ is commonly used in the superelastic materials industry.

In an alternative approach, the hysteresis of the curve may be defined as a ratio of the unloading plateau stress GH to the loading plateau stress CD. Many design engineers adopt this definition of hysteresis in their work with superelastic alloys. Referring to the FIG. 5 example, the hysteresis of the curve under this alternative definition is expressed as the ratio of 55 ksi to 110 ksi, or 1:2. An example of a more preferable hysteresis ratio would be an unloading plateau stress GH of 100 ksi to a loading plateau stress CD of 110 ksi for a smaller hysteresis ratio of 1:1.1. Therefore, the hysteresis of the curve can be defined by the "relative" magnitudes of the loading and unloading plateau stresses.

Under either definition of hysteresis of the curve described above, the present invention seeks to minimize the hysteresis of the superelastic material used to fabricate the expandable strut assembly 14. The expandable strut assembly 14 of the present invention embolic protection device 10 is preferably constructed with a superelastic material having a low loading plateau stress CD relative to the unloading plateau stress GH. This is contrary to the teachings of the prior art.

A higher loading plateau stress CD establishes the mechanical resistance the expandable strut assembly 14 exerts against the delivery system, and specifically the restraining sheath 46. It represents the stress exerted by the expandable strut assembly 14 when it is loaded into restraining sheath 46. A high loading plateau stress relative to the unloading plateau stress is undesirable because of the large and bulky restraining sheath 46 that is needed to deliver the embolic protection device 10.

In FIG. 5, the segment labeled "deploy" represents release of the expandable strut assembly 14 from the delivery sheath 46. Following the arrows, the unloading plateau stress GH represents the stress exerted by the deployed expandable strut assembly 14 against the vessel wall 26. It represents the expanding force available to unfurl the filter element 16, which is one measure of expandable strut performance. When the recovery sheath 48 is moved over the expandable strut assembly 14 to recover the device, the stress follows the segment labeled "recover" in FIG. 5 back to loading plateau stress CD.

Accordingly, the greater the difference (i.e., relative or absolute hysteresis) between the two plateaus CD and GH is, the stronger the delivery system must be to accommodate any given level of expandable strut assembly performance. A stronger delivery system must necessarily be larger and bulkier, with a thicker, more rigid restraining sheath 46. Conversely, reducing the (relative or absolute hysteresis) difference between the two plateaus CD and GH results in smaller hysteresis. The smaller the hysteresis is, the smaller and lower profile the delivery system has to be to accommodate any given level of expandable strut assembly performance.

In accordance with the present invention, the filter assembly 12 requires only a delivery system having a small delivery profile P as illustrated in the cross-sectional view of FIG. 1. Furthermore, the wall thickness of restraining sheath 46 can be reduced as compared to a comparable performance expandable strut assembly 14 not employing the present invention. Such a compact delivery system permits the physician better access and flexibility to reach tortuous arteries and vessels.

In sum, the present invention offers the potential to reduce overall delivery profile defined by loading stress CD for any given level of embolic protection device mechanical performance defined by unloading stress GH. In the present invention, this is accomplished by realizing the properties of superelastic nitinol, preferably in addition with a ternary element, as described in greater detail below.

The superelastic alloy of the present invention is preferably formed from a composition consisting essentially of about 30 to about 52 percent titanium and the balance nickel and up to 15 percent of one or more additional ternary alloying elements. Such ternary alloying elements may be selected from the group consisting of palladium, platinum, chromium, iron, cobalt, vanadium, manganese, boron, copper, aluminum, tungsten, tantalum, or zirconium. In particular, the ternary element may optionally be up to 3 percent each of iron, cobalt, platinum, palladium, and chromium, and up to about 15 percent copper and vanadium. As used herein, all references to percent composition are atomic percent unless otherwise noted.

In another preferred embodiment, a NiTi expandable strut assembly of the embolic protection device with SME (shape memory effect) is heat-treated at approximately 500 degrees C. The expandable strut assembly is mechanically deformed into a first, larger diameter and form for deployment of the filter element. After the filter assembly is exposed within the body lumen after retraction of the restraining sheath, heat at 45 degrees C is applied causing the filter assembly to return to its fully expanded larger diameter and be in contact with the arterial wall of the artery. The application of 45 degrees C of heat is compatible with most applications in the human body, but it is not to be limited to this temperature as higher or lower temperatures are contemplated without departing from the invention. The 45 degrees C temperature can be achieved in a conventional manner well known in the art such as by warm saline injected into the delivery system.

The shape memory characteristics allow the devices to be deformed to facilitate their insertion into a body lumen or cavity and then to be heated within the body so that the device returns to its original shape. Again, alloys having shape memory characterisitcs generally have at least two phases: a martensitic phase, which has a relatively low tensile strength and which is stable at relatively low temperatures, and an austenitic phase, which has a relatively high tensile strength and which is stable at temperatures higher than the martensitic phase.

Shape memory characteristics are imparted to the alloy by heating the metal to a temperature above which the transformation from the martensitic phase to the austenitic phase is complete; i.e., a temperature above which the austenitic phase is stable. The shape of the metal during this heat treatment is the shape "remembered." The heat-treated metal is cooled to a temperature at which the martensitic phase is stable, causing the austenitic phase to transform to the martensitic phase. The metal in the martensitic phase is then plastically deformed, e.g., to facilitate the entry thereof into a patient's body. Subsequent heating of the deformed martensitic phase to a temperature above the martensite to austenite transformation temperature causes the deformed martensitic phase to transform to the austenitic phase. During this phase transformation the metal reverts back to its original shape.

The recovery or transition temperature may be altered by making minor variations in the composition of the metal and in processing the material. In developing the correct composition, biological temperature compatibility must be determined in order to select the correct transition temperature. In other words, when the stent is heated, it must not be so hot that it is incompatible with the surrounding body tissue. Other shape memory materials may also be utilized, such as, but not limited to, irradiated memory polymers such as autocrosslinkable high density polyethylene (HDPEX). Shape memory alloys are known in the art and are discussed in, for example, "Shape Memory Alloys," *Scientific American*, Vol. 281, pp. 74–82 (November 1979).

Shape memory alloys undergo a transition between an austenitic state and a martensitic state at certain temperatures. When they are deformed while in the martensitic state they retain this deformation as long as they are retained in this state, but revert to their original configuration when they are heated to a transition temperature, at which time they transform to their austenitic state. The temperatures at which these transitions occur are affected by the nature of the alloy and the condition of the material. Nickel-titanium-based alloys (NiTi), wherein the transition temperature is slightly lower than body temperature, are preferred for the present invention. It is thus desirable to have the transition temperature set at just below body temperature to insure a rapid transition from the martensitic state to the austenitic state when the embolic protection device of the present invention is deployed in a body lumen.

While the present invention has been illustrated and described herein in terms of superelastic alloy components of a filter assembly of an embolic protection device and its delivery system wherein the superelastic alloy contains a ternary element conferring a small hysteresis, it is apparent to those skilled in the art that the present invention can be used in other instances. Other modifications and improvements may be made without departing from the scope of the present invention.

What is claimed is:

1. An expandable filtering system and a delivery system for deploying the expandable filtering system in a body lumen, comprising:

an expandable strut assembly including a superelastic alloy, wherein the alloy includes a ternary element selected from the group of elements consisting of platinum or tantalum, and wherein the alloy further includes a substantially small stress hysteresis such that a loading plateau is at about 100 to 110 ksi and an unloading plateau is at about 55 to 100 ksi;

a filter element disposed on the expandable strut assembly; and wherein the delivery system includes a sheath having a distal end and a proximal end, wherein the expandable strut assembly is disposed inside the sheath at the distal end, and wherein the delivery system has a small profile.

2. The expandable filtering system and delivery system of claim 1, wherein the superelastic alloy includes a nickel-titanium alloy.

3. The expandable filtering system and delivery system of claim 1, wherein the small stress hysteresis is defined by a curve plotted on right angle axes wherein a y-axis scale represents stress versus an x-axis scale that represents strain, and wherein a Δy of the curve is small.

4. The expandable filtering system and delivery system of claim 1, wherein the small stress hysteresis represents minimal difference between a loading stress and an unloading stress of the alloy.

5. The expandable filtering system and delivery system of claim 1, wherein the sheath includes a thin wall.

6. The expandable filtering system and delivery system of claim 1, wherein the superelastic alloy has a transition temperature set below human body temperature.

7. The expandable filtering system and delivery system of claim 1, wherein the delivery system includes a low profile recovery sheath.

8. The expandable filtering system and delivery system of claim 1, wherein the superelastic alloy has a low loading plateau stress relative to the unloading plateau stress.

9. An expandable filtering system and a delivery system for deploying the expandable filtering system in a body lumen, comprising:

an expandable strut assembly including a nickel-titanium alloy, wherein the nickel-titanium alloy includes a ternary element selected from the group of elements consisting of platinum or tantalum conferring a substantially small stress hysteresis with a loading plateau of about 110 ksi and an unloading plateau of about 55 ksi;

a filter element disposed on the expandable strut assembly;

the delivery system including an inner member having a distal end and a proximal end, wherein the expandable strut assembly is disposed at the distal end; and the delivery system further including a sheath having a distal end and a proximal end, wherein at least the distal end of the sheath is slidably disposed over the expandable strut assembly, and wherein the delivery system has a small profile.

10. The expandable filtering system and delivery system of claim 9, wherein the small stress hysteresis is defined by a curve plotted on right angle axes wherein a y-axis scale represents stress versus an x-axis scale that represents strain, and wherein a $\Delta y$ of the curve is small.

11. The expandable filtering system and delivery system of claim 10, wherein the hysteresis of the curve represents a minimal difference between a loading plateau stress and an unloading plateau stress of the alloy.

12. The expandable filtering system and delivery system of claim 10, wherein the hysteresis of the curve represents a small ratio of an unloading plateau stress relative to a loading plateau stress.

13. The expandable filtering system and delivery system of claim 9, wherein the sheath includes a thin wall.

14. The expandable filtering system and delivery system of claim 9, wherein the alloy includes not more than 15 atomic percent of the ternary element.

15. A method for providing expandable filtering system and a delivery system for deploying the expandable filtering system in a body lumen, comprising:

providing an expandable strut assembly including a nickel-titanium alloy, wherein the nickel-titanium alloy includes a ternary element selected from the group of elements consisting of platinum or tantalum, and wherein the alloy further includes a substantially small stress hysteresis such that the loading plateau is about 100 to 110 ksi and the unloading plateau is about 55 to 100 ksi;

disposing a filter element on the expandable strut assembly;

providing a delivery system including an inner member having a distal end and a proximal end, wherein the delivery system has a small profile;

disposing the expandable strut assembly at the distal end of the delivery system;

providing a sheath as part of the delivery system, the sheath having a distal end and a proximal end; and slidably disposing the sheath over the expandable strut assembly.

16. The method for providing the expandable filtering system and delivery system of claim 15, wherein the step of providing an expandable strut assembly includes defining the small stress hysteresis by a curve plotted on right angle axes wherein a y-axis scale represents stress versus an x-axis scale that represents strain, and wherein a $\Delta y$ of the curve is small.

17. The method for providing the expandable filtering system and delivery system of claim 16, wherein $\Delta y$ of the curve represents the difference between an unloading plateau stress value and a loading plateau stress value.

18. An expandable filtering system and a delivery system for deploying the expandable filtering system in a body lumen, comprising:

an expandable strut assembly including a superelastic alloy, the superelastic alloy having a ternary element wherein the superelastic alloy includes approximately 30 to 52 atomic percent titanium, at least 38 atomic percent nickel, and up to 15 atomic percent of a ternary element selected from the group of elements consisting of platinum or tantalum, and conferring a substantially small stress hysteresis such that the loading plateau is about 100 ksi and the unloading plateau is about 55 ksi;

a filter element disposed on the expandable strut assembly; and wherein the delivery system includes a sheath having a distal end and a proximal end, wherein the expandable strut assembly is disposed inside the sheath at the distal end, and wherein the delivery system has a small profile.

* * * * *